United States Patent
Vestergaard et al.

(10) Patent No.: US 7,288,785 B2
(45) Date of Patent: Oct. 30, 2007

(54) SUBSTRATE AND METHOD FOR MEASURING THE ELECTRO-PHYSIOLOGICAL PROPERTIES OF CELL MEMBRANES

(75) Inventors: Ras Kaas Vestergaard, Copenhagen (DK); Niels Willumsen, Copenhagen (DK); Nicholas Oswald, Edinburgh (GB); Jonatan Kutchinsky, Ballerup (DK); Dirk Reuter, Göttingen (DE); Rafael Taboryski, Lyngby (DK)

(73) Assignee: Sophion Bioscience A/S, Ballerup (DK)

( * ) Notice: Subject to any disclaimer, the term of this patent is extended or adjusted under 35 U.S.C. 154(b) by 304 days.

(21) Appl. No.: 10/417,327

(22) Filed: Apr. 17, 2003

(65) Prior Publication Data

US 2004/0005696 A1    Jan. 8, 2004

Related U.S. Application Data

(60) Provisional application No. 60/372,796, filed on Apr. 17, 2002.

(30) Foreign Application Priority Data

Feb. 21, 2003  (GB) ................................. 0303922.9

(51) Int. Cl.
*H01L 29/10* (2006.01)
*C12M 1/34* (2006.01)

(52) U.S. Cl. ............... 257/48; 257/E51.045; 435/285.2; 435/287.1

(58) Field of Classification Search ............ 435/287.1, 435/258.2; 204/430.01; 257/48, E51.045
See application file for complete search history.

(56) References Cited

U.S. PATENT DOCUMENTS

| 5,047,215 | A  | * | 9/1991  | Manns ....................... 422/101 |
| 5,501,893 | A  |   | 3/1996  | Laermer et al. |
| 6,863,833 | B1 | * | 3/2005  | Bloom et al. ................... 216/2 |
| 2002/0164777 | A1 | * | 11/2002 | Kelly et al. ............. 435/287.1 |
| 2003/0107386 | A1 | * | 6/2003  | Dodgson et al. ............ 324/699 |
| 2003/0121778 | A1 | * | 7/2003  | Dodgson et al. ............ 204/401 |
| 2004/0120854 | A1 | * | 6/2004  | Heath et al. .................. 422/57 |

FOREIGN PATENT DOCUMENTS

DE    4241045 C1    5/1994
DE    297 21 359    2/1998

(Continued)

OTHER PUBLICATIONS

Mayer, M., "Screening for Bioactive Compounds: Chip-Based Functional Analysis of Single Ion Channels & Capillary Electrochomatography for Immunoaffinity Selection"; Ph.D. Thesis, Lausanne (2000).

(Continued)

*Primary Examiner*—W. David Coleman
(74) *Attorney, Agent, or Firm*—Birch, Stewart, Kolasch & Birch, LLP

(57) ABSTRACT

The present invention relates to a substantially planar substrate for use in patch clamp analysis of the electrophysiological properties of a cell membrane comprising a glycocalyx, wherein the substrate comprises an aperture having a rim, the rim being adapted to form a gigaseal upon contact with the cell membrane, The invention further provides a method of making such a substrate and method for analysing the electrophysiological properties of a cell membrane comprising a glycocalyx.

25 Claims, 11 Drawing Sheets

FOREIGN PATENT DOCUMENTS

| WO | WO94/14187 | 6/1994 |
|----|------------|--------|
| WO | WO-99/31503 | 6/1999 |
| WO | WO-00/71742 A2 | 11/2000 |
| WO | WO-01/25769 | 4/2001 |
| WO | WO-01/48474 | 7/2001 |
| WO | WO 02/066596 A2 | 8/2002 |
| WO | WO 02/077259 A2 | 10/2002 |
| WO | WO 03/089564 A1 | 10/2003 |

OTHER PUBLICATIONS

Neher, E., Nature Biotechnology, vol. 19, p. 114 (2001).

Penner, R., Chapter 1: "A Practical Guide to Patch Clamping", *Single-Channel Recording*. Plenum Press, New York, pp. 3-30 (1995).

Rae, J.L. et al., "Glass Technology for Patch Clamp Clectrodes"; *Methods in Enzymology*, vol. 207, pp. 66-92 (1992).

Simons, K. et al., "Lipid Rafts and Signal Transduction", Nature Reviews, vol. 1, pp. 31-41 (2000).

Madou, M., "Fundamentals of Microfabrication", CRC Press, 2nd Ed. (Dec. 2001), ISBN: 0849308267.

Neher, E. et al., "The Extracellular Patch Clamp: A Method for Resolving Currents Through Individual Open Channels in Biological Membranes", Pflügers Arch., No. 375, pp. 219-228 (1978).

Hamil, O.P. et al., "Improved Patch-Clamp Techniques for High-Resolution Current Recording from Cells and Cell-Free Membrane Patches", Pflügers Arch., No. 391, pp. 85-100 (1981).

Christopher Miller (1986), Ion Channel Reconstitution, Plenum Press, Title Page, Table of Contents. (13 pages).

Schmidt, C. et al., Angewandte Chemie. International Edition, vol. 39, No. 3137, (2000), pp. 3137-3140.

* cited by examiner

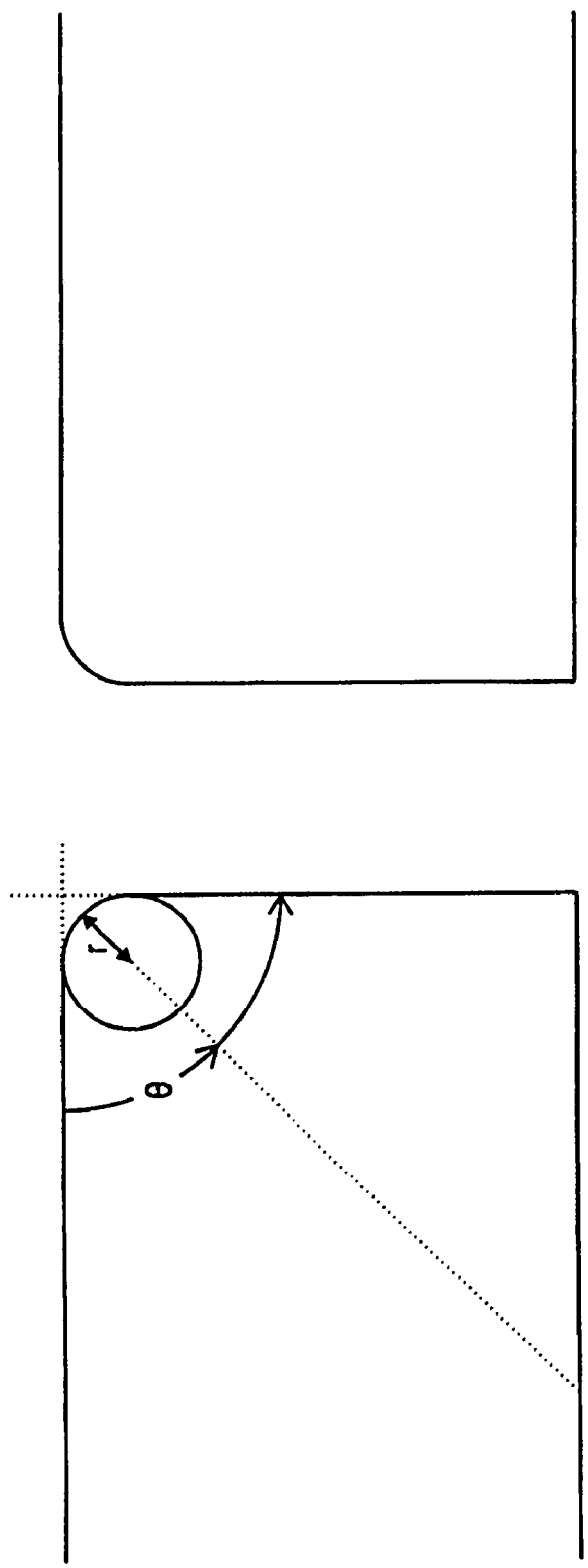

SUBSTRATE AND METHOD FOR MEASURING THE ELECTRO-PHYSIOLOGICAL PROPERTIES OF CELL MEMBRANES This application claims priority on provisional Application No. 60/372,796 filed on Apr. 17, 2002, the entire contents of which are hereby incorporated by reference.

TECHNICAL FIELD

The present invention provides a substrate and a method for determining and/or monitoring electrophysiological properties of ion channels in ion channel-containing structures, typically lipid membrane-containing structures such as cells, by establishing an electrophysiological measuring configuration in which a cell membrane forms a high resistive seal around a measuring electrode, making it possible to determine and monitor a current flow through the cell membrane. More particularly, the invention relates to a substrate and a method for analysing the electrophysiological properties of a cell membrane comprising a glycocalyx. The substrate is typically part of an apparatus for studying electrical events in cell membranes, such as an apparatus for carrying out patch clamp techniques utilised to study ion transfer channels in biological membranes.

BACKGROUND OF THE INVENTION

Introduction

The general idea of electrically insulating a patch of membrane and studying the ion channels in that patch under voltage-clamp conditions is outlined in Neher, Sakmann, and Steinback (1978) "The Extracellular Patch Clamp, A Method For Resolving Currents Through Individual Open Channels In Biological Membranes", Pflüger Arch. 375; 219–278. It was found that, by pressing a pipette containing acetylcholine (ACh) against the surface of a muscle cell membrane, one could see discrete jumps in electrical current that were attributable to the opening and closing of ACh-activated ion channels. However, the researchers were limited in their work by the fact that the resistance of the seal between the glass of the pipette and the membrane (10–50 MΩ) was very small relative to the resistance of the channel (10 GΩ). The electrical noise resulting from such a seal is inversely related to the resistance and, consequently, was large enough to obscure the currents flowing through ion channels, the conductance of which are smaller than that of the ACh channel. It also prohibited the clamping of the voltage in the pipette to values different from that of the bath due to the resulting large currents through the seal.

It was then discovered that by fire polishing the glass pipettes and by applying suction to the interior of the pipette a seal of very high resistance (1 to 100 GΩ) could be obtained with the surface of the cell, thereby reducing the noise by an order of magnitude to levels at which most channels of biological interest can be studied and greatly extended the voltage range over which these studies could be made. This improved seal has been termed a 'gigaseal', and the pipette has been termed a 'patch pipette'. A more detailed description of the gigaseal may be found in O. P. Hamill, A. Marty, E. Neher, B. Sakmann & F. J. Sigworth (1981) "Improved patch-clamp techniques for high resolution current recordings from cells and cell-free membrane patches." Pflügers Arch. 391, 85–100. For their work in developing the patch clamp technique, Neher and Sakmann were awarded the 1991 Nobel Prize in Physiology and Medicine.

Ion channels are transmembrane proteins which catalyse transport of inorganic ions across cell membranes. The ion channels participate in processes as diverse as generating and timing action potentials, synaptic transmission, secretion of hormones, contraction of muscles, etc. Many pharmacological agents exert their specific effects via modulation of ion channels. Examples include antiepileptic compounds such as phenytoin and lamotrigine, which block voltage-dependent Na+-channels in the brain, antihypertensive drugs such as nifedipine and diltiazem, which block voltage dependent Ca2+-channels in smooth muscle cells, and stimulators of insulin release such as glibenclamide and tolbutamide, which block an ATP-regulated K+-channel in the pancreas. In addition to chemically-induced modulation of ion-channel activity, the patch clamp technique has enabled scientists to perform manipulations with voltage-dependent channels. These techniques include adjusting the polarity of the electrode in the patch pipette and altering the saline composition to moderate the free ion levels in the bath solution.

The Patch Clamp Technique

The patch clamp technique represents a major development in biology and medicine, since it enables measurement of ion flow through single ion channel proteins, and also enables the study of a single ion channel activity in response to drug exposure. Briefly, in standard patch clamping, a thin (approx. 0.5–2 μm in diameter) glass pipette is used. The tip of this patch pipette is pressed against the surface of the cell membrane. The pipette tip seals tightly to the cell membrane and isolates a small population of ion channel proteins in the tiny patch of membrane limited by the pipette orifice. The activity of these channels can be measured individually ('single channel recording') or, alternatively, the patch can be ruptured, allowing measurements of the channel activity of the entire cell membrane ('whole-cell configuration'). High-conductance access to the cell interior for performing whole-cell measurements can be obtained by rupturing the membrane by applying negative pressure in the pipette.

The Gigaseal

As discussed above, an important requirement for patch clamp measurements of single-channel currents is the establishment of a high-resistance seal between the cell membrane and the glass micropipette tip, in order to restrict ions from moving in the space between the two surfaces. Typically, resistances in excess of 1 GΩ are required, hence the physical contact zone is referred to as a 'gigaseal'.

Formation of a gigaseal requires that the cell membrane and the pipette glass are brought into close proximity to each other. Thus, while the distance between adjacent cells in tissues or between cultured cells and their substrates generally is in the order of 20–40 nm (Neher, 2001), the distance between the cell membrane and the pipette glass in the gigaseal is predicted to be in the Angstrom (i.e. 10–10 m) range. The physico-chemical nature of the gigaseal is not known. However, gigaseals may be formed between cell membranes and a wide variety of glass types including quartz, aluminosilicate, and borosilicate (Rae and Levis, 1992), indicating that the specific chemical composition of the glass is not crucial.

Cell Membrane Structure

Cell membranes are composed of a phospholipid bilayer with intercalated glycoproteins, the latter serving a multitude of functions including acting as receptors for various agents. These membrane-spanning glycoproteins typically comprise peptide- and glyco-moieties which extend out from the membrane into the extracellular space, forming a so-called 'glycocalyx' layer around the phospholipid bilayer which reaches a height of 20 to 50 nm and creates an electrolyte-filled compartment adjacent to the phospholipid bilayer (see FIG. 1). Thus, the glycocalyx forms a hydrophilic and negatively charged domain constituting the interspace between the cell and its aqueous environment.

Cytoskeleton and Glycocalyx

Immediately underneath the cell membrane is located the cytoskeleton, a meshwork of actin filaments, spectrin, anchyrin, and a multitude of other large structural molecules. One important role of the cytoskeleton is to anchor certain integral membrane proteins and glycoproteins to fixed positions within the membrane. However, it is believed that intercalated membrane glycoproteins are free, within certain limits (lipid micro domains or 'rafts'; for a review see Simons and Toomre, 2000), to move laterally in the phospholipid bilayer. Indeed, such an arrangement has been described as being 'like protein icebergs in an ocean of lipids'.

Effect of Glycocalyx on Gigaseal Formation

In conventional patch clamp methods, the initial point of contact between the glass pipette tip (which has a wall thickness of approximately 100 nm) and the cell involves the glycocalyx. An estimation of the electrical resistance, represented by the 150 mM electrolyte contained in the interspace defined between the glass surface and the lipid membrane, by the height of the glycocalyx (e.g. 20 to 40 mn) results in 20–60MΩ. This estimation is in agreement with experimental observations on smooth surface quartz coated chips of the TEOS (Triethyloxysilane) type, which routinely yield resistances in the order of 40 MΩ (or only 4% of a GΩ). In this estimation, it is assumed that the electrolyte is present between the lipid membrane and a glass surface approximately of cylindrical shape with diameter about 1 μm and length about 3–10 μm. Subsequent gentle suction (<20 hPa) applied to the pipette further increases the resistance, ideally leading to a gigaseal. Gigaseal formation may take place rapidly on a time scale of 0.1 to 10 s, or it may be a prolonged process completed only after several successive rounds of increased suction pressure. The time course of the gigaseal formation, reflects the exclusion of glycoproteins from the area of physical (membrane/pipette) contact by lateral displacement in the 'liquid-crystal' phospholipid bilayer. In other words, the elements of the glycocalyx, i.e. glycoproteins, are squeezed out of the area of contact due to the negative hydrostatic pressure applied to the pipette which forces the phospholipid bilayer (the hydrophilic polar heads of the phospholipids) against the glass surface (hyydrophilic silanol groups).

However, sometimes the process of resistance increase proceeds only up to formation of a quasi gigaseal (0.5 to 1 GΩ). Empirically, application of a large (50–70 mV; Penner, 1995) negative electrical potential to the pipette at this point may lead to the final resistance increase terminating with the gigaseal. In terms of the glycocalyx, the latter observation may be explained by negatively charged domains of glycoproteins being displaced laterally driven by the applied negative pipette potential. The strength of the electrical field (E) acting on the glycoproteins, i.e. the electrical field from pipette lumen to the surrounding bath is considerable:

$$E = \frac{x}{V} = \frac{70 \text{ mV}}{100 \text{ nm}} = 700.000 \text{ V/m}$$

assuming a pipette tip wall thickness (x) of 100 nm and an applied pipette potential (V) of –70 mV.

Conventional Pipettes Versus Planar Substrates

Recent developments in patch clamp methodology have seen the introduction of planar substrates (e.g. a silicon chip) in place of conventional glass micropipettes (for example, see WO 01/25769 and Mayer, 2000).

Attempts to form gigaseals between planar silicon-based chips and living cells have proven problematic (for example, see Mayer, 2000). However, success has been achieved in obtaining gigaseals between artificial phospholipid vesicles which contain no exterior glycocalyx. This finding indicates a critical importance of the glycocalyx in the gigaseal formation process.

Hence, there is a need for improved planar substrates suitable for use in patch clamp studies of cell membrane electrophysiology which permit the formation of a gigaseal with cell membranes comprising a glycocalyx.

SUMMARY OF THE INVENTION

The present invention provides a substrate and a method optimised for determining and/or monitoring current flow trough an ion channel-containing structure, in particular a cell membrane having a glycocalyx, under conditions that are realistic with respect to the influences to which the cells or cell membranes are subjected. Thus, data obtained using the substrate and the method of the invention, such as variations in ion channel activity as a result of influencing the cell membrane with, e.g. various test compounds, call be relied upon as true manifestations of the influences proper and not of artefacts introduced by the measuring system, and can be used as a valid basis for studying electrophysiological phenomena related to the conductivity or capacitance of cell membranes under given conditions.

It will be understood that when the term 'cell' or 'cell membrane' is used in the present specification, it will normally, depending on the context, be possible to use any other ion channel-containing structure, such as another ion channel-containing lipid membrane or an ion channel-containing artificial membrane.

As discussed above, an important requirement for patch clamp measurements of single-channel currents is the establishment of a high-resistance gigaseal between the cell membrane and the substrate. A key factor in formation of a gigaseal is the proximity of the cell membrane to the substrate, which is turn is dependent on the size of the area of contact between the cell membrane and the substrate.

The physical area of contact between the cell membrane and a planar silicon chip (about 1 μm width of contact rim; see FIG. 2, right hand diagram) with a smoothly rounded, funnel-like orifice is much larger than that formed between a cell membrane and a glass micropipette (about 100 nm width; FIG. 2, left hand diagram). This results in the force per unit area being considerably reduced in the chip relative to the pipette configuration, and the number of intercalated glycoproteins in the contact area being much larger, effectively preventing the required Angström distance between the phospholipid bilayer and the substrate surface imperative for the formation of a gigaseal The present invention seeks to address this problem by providing a planar substrate (e.g. a silicon-based chip), suitable for patch clamp studies of the electrophysiological properties of cell membrane, which is designed to provide a reduced area of contact with the cell membrane, thereby promoting the formation of a gigaseal.

Thus, a first aspect of the invention provides a substantially planar substrate for use in patch clamp analysis of the electrophysiological properties of a cell membrane comprising a glycocalyx, wherein the substrate comprises an aperture having a rim defining the aperture, the rim being adapted to form a gigaseal upon contact with the cell membrane.

In a preferred embodiment, the substrate is a silicon-based chip.

In the present context, the term gigaseal normally indicates a seal of a least 1G ohm, and this is the size of seal normally aimed at as a minimum, but for certain types of measurements where the currents are large, lower values may be sufficient as threshold values.

By 'glycocalyx' we mean the layer created by the peptide- and glyco-moieties, which extend into the extracellular space from the glycoproteins in the lipid bilayer of the cell membrane.

Preferably, the rim protrudes from the plane of the substrate to a length in excess of the height of the glycocalyx above the phospholipid bilayer of the cell membrane. More preferably, the rim extends at least 20 nm, at least 30 nm, at least 40 nm, at least 50 nm, at least 60 nm, at least 70 nm, at least 80 nm, at least 90 nm or at least 100 nm above the plane of the substrate Advantageously, the rim is shaped such that the area of physical contact between the substrate and the cell membrane is minimised, thereby favouring penetration of the glycocalyx and formation of a gigaseal.

It will be appreciated by persons skilled in the art that the rim may be of any suitable cross-sectional profile. For example, the walls of the rim may be tapered or substantially parallel . Likewise, the uppermost tip of the rim may take several shapes, for example it may be dome-shaped, flat or pointed. Furthermore, the rim protrusion may be substantially perpendicular to, oblique, or parallel with the plane of the substrate. A parallel protruding rim may be located at or near to the mouth of the aperture or, alternatively, positioned deeper into the aperture. Conveniently, the width of the rim is between 10 and 200 nm.

Alternatively the rim is formed by the mouth of the aperture itself, rather from a protrusion. The mouth of the aperture may be sharp with a radius of curvature between 5 and 100 nm with an angle of 45 to 90 degrees.

It will be further appreciated by persons skilled in the art that the aperture should have dimensions which do not permit an intact cell to pass through the planar substrate.

Preferably, the length (i.e. depth) of the aperture is between 2 and 30 µm, for example between 2 and 20 µm, 2 and 10 µm, or 5 and 10 µm.

The optimal diameter of the aperture for optimal gigaseal formation and whole cell establishment will be dependent on the specific cell type being used. Advantageously, the diameter of the aperture is in the range 0.5 to 2 µm.

The substrate of the invention will typically be a component used in an apparatus for carrying out measurements of the electrophysiological properties of ion transfer channels in lipid membranes such as cells.

The apparatus may be designed to provide means for carrying out a large number of individual experiments in a short period of time. This is accomplished by providing a microsystem having a plurality of test confinements (i.e. rimmed apertures for contacting cells) each of which having sites comprising integrated measuring electrodes, and providing and suitable test sample supply. Each test confinement may comprise means for positioning cells, for establishment of gigaseal, for selection of sites at which giga-seal has been established, measuring electrodes and one or more reference electrodes. Thereby it is possible to perform independent experiments in each test confinement, and to control the preparation and measurements of all experiments from a central control unit such as a computer. Due to the small size of the test confinements, the invention permits carrying out measurements utilising only small amounts of supporting liquid and test sample.

The substrate of the invention can be made of any material suitable for a wafer processing technology, such as silicon, plastics, pure silica and other glasses such as quartz and Pyrex™ or silica doped with one or more dopants selected from the group of Be, Mg, Ca, B, Al, Ga, Ge, N, P, As. Silicon is the preferred substrate material.

In a preferred embodiment of the first aspect of the invention, the surface of the substrate and/or the walls of the aperture are coated with a material that is well suited for creating a seal with the cell membrane. Such materials include silicon, plastics, pure silica and other glasses such as quartz and Pyrex™ or silica doped with one or more dopants selected from the group of Be, Mg, Ca, B, Al, Ga, Ge, N, P, As and oxides from any of these. Preferably, the substrate is coated, at least in part, with silicon oxide.

In a further preferred embodiment of the first aspect of the invention, the planar substrate has a first surface part and an opposite second surface part, the first surface part having at least one site adapted to hold an ion channel-containing structure, each site comprising an aperture with a rim and having a measuring electrode associated therewith, the substrate carrying one or more reference electrodes, the measuring electrodes and the reference electrodes being located in compartments filled with electrolytes on each side of the aperture, the measuring electrodes and the respective reference electrode or reference electrodes being electrodes capable of generating, when in electrolytic contact with each other and when a potential difference is applied between them, a current between them by delivery of ions by one electrode and receipt of ions by the other electrode, each of the sites being adapted to provide a high electrical resistance seal between an ion channel-containing structure held at the site and a surface part of the site, the seal, when provided, separating a domain defined on one side of the ion channel-containing structure and in electrolytic contact with the measuring electrode from a domain defined on the other side of the ion channel-containing structure and in electrolytic contact with the respective reference electrode so that a current flowing through ion channels of the ion channel-containing structure between the electrodes can be determined and/or monitored, the electrodes being located on each side of the substrate.

Examples of the general design of the preferred embodiment of the first aspect of the invention wherein the substrate comprises integral electrodes (but without the rimmed aperture feature of the present invention) are described in WO 01/25769.

A second aspect of the invention provides a method for making a substrate according to the first aspect of the invention, the method comprising the steps of
(i) providing a substrate template;
(ii) forming an aperture in the template; and
(iii) forming a rim around the aperture.

Preferably, the substrate is manufactured using silicon micro fabrication technology "Madou, M., 2001".

It will be appreciated by persons skilled in the art that steps (ii) and (iii) may be performed sequentially (i.e. in temporally separate steps) or at the same time.

Advantageously, step (ii) comprises forming an aperture by use of an inductively coupled plasma (ICP) deep reactive ion etch process. "Laermer F. and Schilp, A., DE4241045"

When it is required to form a substantially vertical protrusion relative to the plane of the substrate, the method comprises an intermediate step of a directional and selective etching of the front side of the substrate causing a removal of a masking layer on the front side of the substrate, and further proceeding the prescribed protrusion distance into the underlying substrate.

As a result of a faster etch rate of silicon compared to that of the masking material, the masking material will be left inside the aperture, and protrude from the surface. An overall surface coating can subsequently be applied.

When it is required to form a protrusion lying substantially in the plane of the substrate, the method comprises an intermediate step of using Inductively Coupled Plasma (ICP) etch or Advanced Silicon Etch (ASE) for the formation of the pore, where the repetitive alternation of etching and passivation steps characterising these methods, will result in some scalloping towards the mouth of the aperture. By suitable adjustment of the process parameters, the scalloping can result in an inward in plane protrusion of the rim.

Again, an overall surface coating can subsequently be employed.

Conveniently, the method further comprises coating the surface of the substrate (e.g. with silicon oxide), either before or after formation of the aperture and/or rim. Alternatively, step (iii) is performed at the same time as coating the substrate.

Such coatings may be deposited by use of plasma enhanced chemical vapour deposition (PECVD) and/or by use of low pressure chemical vapour deposition (LPCVD).

The preferred embodiment of the first aspect of the invention wherein the substrate comprises integral electrodes may be manufactured as described in WO 01/25769).

A third aspect of the invention provides a method for analysing the electrophysiological properties of a cell membrane comprising a glycocalyx, the method comprising
  (i) providing a substrate having a rimmed aperture according to the first aspect of the invention;
  (ii) contacting the cell membrane with the rim of an aperture of the substrate such that a gigaseal is formed between the cell membrane and the substrate; and
  (iii) measuring the electrophysiological properties of the cell membrane.

In a preferred embodiment of the third aspect of the invention, there is provided a method of establishing a whole cell measuring configuration for determining and/or monitoring an electrophysiological property of one or more ion channels of one or more ion channel-containing structures, said method comprising the steps of:
  (i) providing a substrate as defined above;
  (ii) supplying a carrier liquid at one or more apertures, said carrier liquid containing one or more ion channel-containing structures;
  (iii) positioning at least one of the ion channel-containing structures at a corresponding number of apertures;
  (iv) checking for a high electrical resistance seal between an ion channel-containing structure held at a site (i.e. aperture) and the surface part of the site (i.e. rim) with which the high electrical resistance seal is to be provided by successively applying a first electric potential difference between the measuring electrode associated with the site and a reference electrode, monitoring a first current flowing between said measuring electrode and said reference electrode, and comparing said first current to a predetermined threshold current and, if the first current is at most the predetermined threshold current, then approving the site as having an acceptable seal between the ion channel-containing structure and the surface part of the site; and
  (v) establishing a whole-cell configuration at approved site(s), whereby a third current flowing through ion channels of the ion channel-containing structure between the measuring electrode and the reference electrodes can be determined and/or monitored.

An ion channel-containing structure (e.g. a cell) in a solution may be guided towards a site on a substrate either by active or passive means. When the ion channel-containing structure makes contact with aperture rim, the contact surfaces form a high electrical resistance seal (a gigaseal) at the site, such that an electrophysiological property of the ion channels can be measured using electrodes. Such an electrophysiological property may be current conducted through the part of membrane of the ion channel-containing structure that is encircled by the gigaseal.

A whole-cell configuration may be obtained by applying, between the measuring electrode associated with each approved site and a reference electrode, a series of second electric potential difference pulses, monitoring a second current flowing between the measuring electrode and the reference electrode, and interrupting the series of second electric potential difference pulses whenever said second current exceeds a predetermined threshold value, thereby rupturing the part of the ion channel-containing structure which is closest to the measuring electrode.

Alternatively, the whole-cell configuration may be obtained by subjecting the part of the ion channel-containing structure which is closest to the measuring electrode to interaction with a aperture forming substance.

It should be noted that in the present context, the term "whole-cell configuration" denotes not only configurations in which a whole cell has been brought in contact with the substrate at a measuring site and has been punctured or, by means of a aperture-forming substance, has been opened to electrical contact with the cell interior, but also configurations in which an excised cell membrane patch has been arranged so that the outer face of the membrane faces "upwardly", towards a test sample to be applied.

As the measuring electrode associated with a site may be one of a plurality of electrodes on the substrate, and the ion channel-containing structure may be one of many in a solution, it is possible to obtain many such prepared measuring set-ups on a substrate. A typical measurement comprises adding a specific test sample to the set-up, for which reason each measuring set-up is separated from other measuring set-ups to avoid mixing of test samples and electrical conduction in between set-ups.

In use, the addition of cell-supporting liquid and cells to the substrate is carried out in one of the following ways. In a preferred embodiment, the test confinements are accessible from above, and droplets of supporting liquid and cells can be supplied at each test confinement by means of a dispensing or pipetting system. Systems such as an ink jet printer head or a bubble jet printer head can be used. Another possibility is an nQUAD aspirate dispenser or any other dispensing/pipetting device adapted to dose small amounts of liquid. Alternatively, supporting liquid and cells are applied on the substrate as a whole (e.g. by pouring supporting liquid containing cells over the substrate or immersing the substrate in such), thereby providing supporting liquid and cells to each test confinement. Since the volumes of supporting liquid and later test samples are as small as nanolitres, water vaporisation could represent a problem. Therefore, depending of the specific volumes, handling of liquids on the substrate should preferably be carried out in high humidity atmospheres.

In another embodiment, the cells are cultivated directly on the substrate, while immersed in growth medium. In the optimal case, the cells will form a homogeneous monolayer (depending on the type of cells to be grown) on the entire surface, except at regions where the surface intentionally is made unsuitable for cell growth, The success of cultivation of cells on the substrate depends strongly on the substrate material.

In still another embodiment, an artificial membrane with incorporated ion channels may be used instead of a cell. Such artificial membrane can be made from a saturated solution of lipids, by positioning a small lump of lipid over an aperture. This technique is thoroughly described by Christopher Miller (1986) Ion Channel Reconstitution, Plenum 1986, p. 577. If the aperture size is appropriate, and a polar liquid such as water is present on both sides of the aperture, a lipid bilayer can form over the aperture. The next step is to incorporate a protein ion channel into the bilayer. This can be achieved by supplying lipid vesicles with incorporated ion channels on one side of the bilayer. The vesicles can be drawn to fusion with the bilayer by e.g. osmotic gradients, whereby the ion channels are incorporated into the bilayer.

Obtaining good contact between the cell and a glass pipette, and thereby creating a gigaseal between a cell and the tip the pipette, is well described in the prior art. In order to draw the cell to the tip of the pipette, as well as to make the necessary contact for obtaining the gigaseal, it is normal to apply suction to the pipette. However, with the planar substrates of the present invention mere contact between the cell membrane and the substrate, typically ultra-pure silica, can be sufficient for the cell to make some bonding to the surface and create a gigaseal.

The positioning of a cell over an aperture in the substrate can be carried out by electrophoresis, where an electric field from an electrode draws the charged cell towards it. Negatively charged cells will be drawn towards positive electrodes and vice versa. The electrostatic pull can also act as guiding means for a group of electrodes. Alternatively, within a test confinement, a hydrophobic material may cover the surface of the substrate except at areas just around electrodes. Thereby, cells can only bind themselves on electrode sites. It is possible to apply both of these methods simultaneously or optionally in combination with a suitable geometrical shape of the substrate surface around electrodes, to guide the sinking cells towards the electrode.

Alternatively, the positioning of a cell over an aperture in the substrate can be carried out by electro-osmosis.

If suction is applied, it draws the cell to the aperture and establishes a connection between the cell and the aperture, creating a gigaseal separating the aperture inside and the solution. The gigaseal may take any form, e.g. circular, oval or rectangular. Where the substrate comprises integral electrodes, the supporting liquid may make electrical contact between the cell membrane and a reference electrode. The cell may be deformed by the suction, and a case where the cell extends into (but does not pass through) the aperture may be desired if controlled.

Using the substrates and methods of the invention, the activity of the ion channels in the cell membrane can be measured electrically (single channel recording) or, alternatively, the patch can be ruptured allowing measurements of the channel activity of the entire cell membrane (whole cell recording). High-conductance access to the cell interior for performing whole cell measurements can be obtained in at least three different ways (all methods are feasible, but various cells may work better with different approaches):

(a) The membrane can be ruptured by suction from the aperture side. Subatmospheric pressures are applied either as short pulses of increasing strength or as ramps or steps of increasing strength. Membrane rupture is detected by highly increased capacitative current spikes (reflecting the total cell membrane capacitance) in response to a given voltage test pulse;

(b) Membrane rupture by applied voltage pulses. Voltage pulses are applied either as short pulses of increasing strength (mV to V) and duration (μs to ms), or as ramps or steps of increasing strength, between the electrodes. The lipids forming the membrane of a typical cell will be influenced by the large electrical field strength from the voltage pulses, whereby the membrane to disintegrates in the vicinity of the electrode, Membrane rupture is detected by highly increased capacitative current spikes in response to a given voltage test pulse.

(c) Permeabilization of membrane. Application of aperture-forming substances (for example antibiotics such as nystatin or amphotericin B), by e.g. prior deposition of these at the site. Rather than by rupturing the membrane, the membrane resistance is selectively lowered by incorporation of permeabilizing molecules, resulting in effective cell voltage control via the electrode pair. The incorporation is followed by a gradually decreasing total resistance and an increasing capacitance.

Where the substrate comprises a plurality test confinements each comprising an aperture, test samples may be added to each test confinement individually, with different test samples for each test confinement. This can be carried out using the methods for applying supporting liquid, with the exception of the methods where supporting liquid are applied on the substrate as a whole.

Upon positioning the cell in a measuring configuration, several electrophysiological properties can be measured, such as current through ion channels (voltage clamp), or capacitance of ion channels containing membranes. In any case, a suitable electronic measuring circuit should be provided. The person skilled in the art will be able to select such suitable measuring circuit.

A fourth aspect of the invention provides a kit for performing a method according to the third aspect of the invention, the kit comprising a substrate according to the first aspect of the invention and one or more media or reagents for performing patch clamp studies.

Preferably the kit comprises a plurality of substrates.

BRIEF DESCRIPTION OF THE DRAWING FIGURES

The invention will now be described with reference to the following non-limiting examples and figures:

FIG. 9 shows a design without protrusion but with a rim sufficiently sharp (r=25–100 nm) to reduce the membrane/substrate contact zone to 50–200 nm. The aperture angle (θ) is 45 to 90 degrees;

DETAILED DESCRIPTION OF THE PREFERRED EMBODIMENTS

EXAMPLES

The present invention identifies three factors that are important for gigaseal formation and whole cell establishment in patch clamp measurements performed on living cells containing glycocalyx in the cell membrane:
1. The length of the aperture should be sufficiently long in order to prevent the relatively elastic cells to be moved through the orifice upon application of suction.
2. There also appears to exist an optimal aperture size for gigaseal formation and whole cell establishment which relates to the elastic properties of the cell membrane and the cell type being studied.
3. The aperture of the planar substrate should be defined by a rim capable of displacing the glycocalyx when approaching the cell surface.

Each factor is discussed below:

Length of the Aperture

The length (i.e. depth) of the aperture, defined by the membrane thickness of the chip, is also important. Low aspect ratio designs (short apertures) suffer from the disadvantage that cells, upon positioning and subsequent suction, have a tendency to move through the hole due to their inherent elasticity. Studies have demonstrated that this problem may be effectively obviated by using longer apertures, typically in excess of 2 μm (data not shown).

Determination of Optimal Aperture Size

Figure 1:
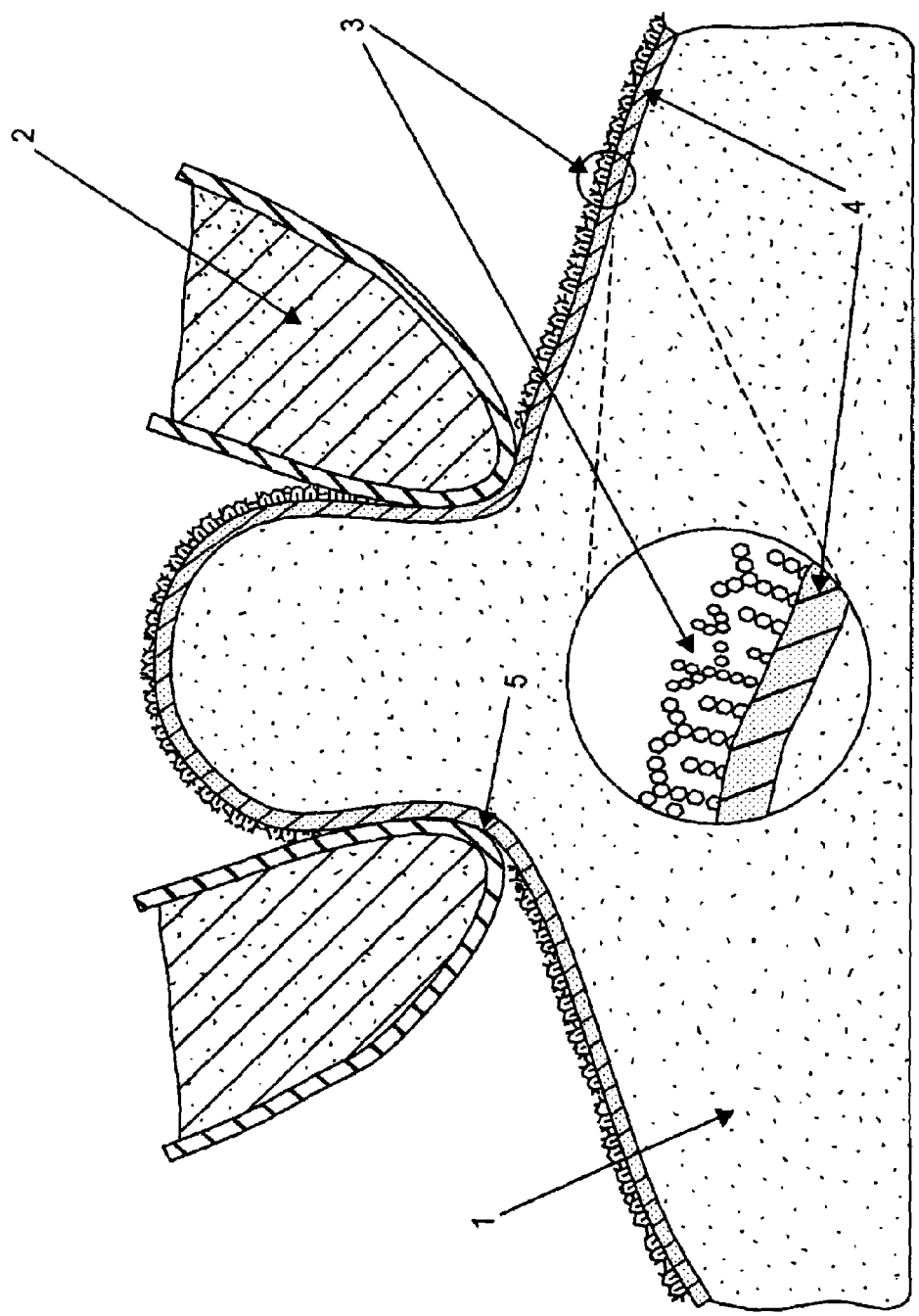
FIG. 1 shows the cell with a patch pipette attached. In the gigaseal zone, (indicated by shaded area at point of contact between the pipette tip and the cell membrane) the glycoproteins of the glycocalyx have been displaced laterally to allow direct contact between the membrane phospholipid bilayer and the pipette.
Figure 2:
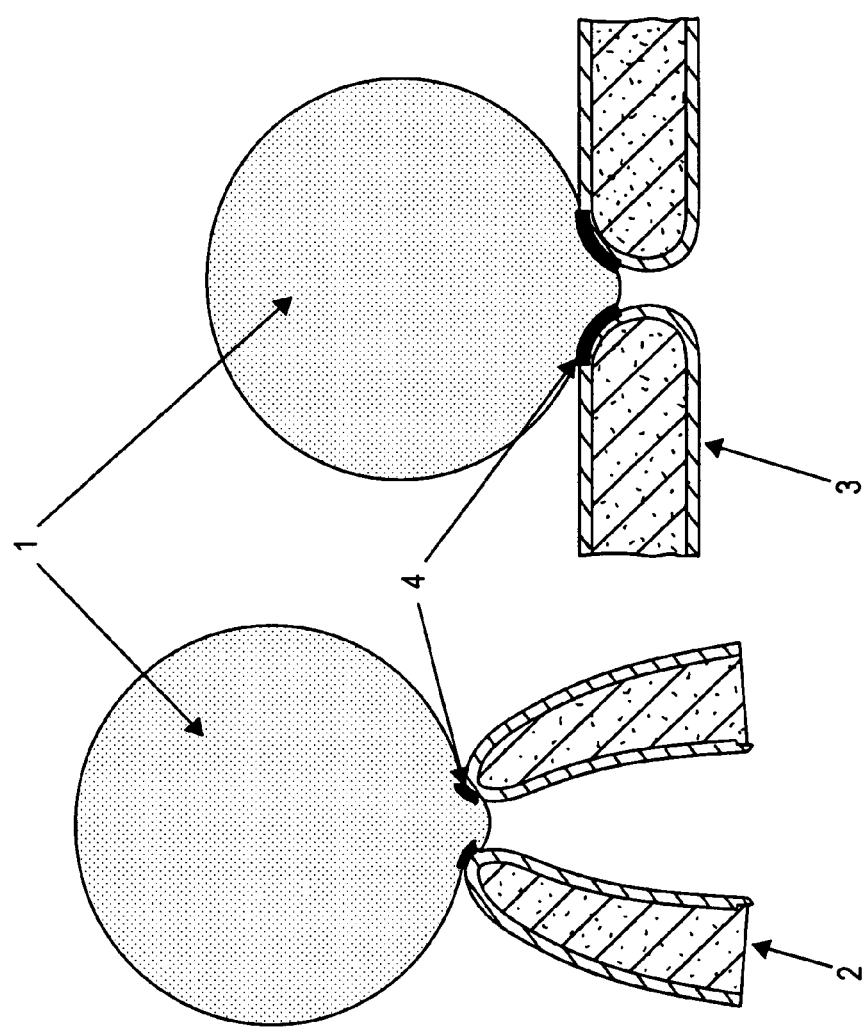
FIGS. 2a and 2b show a cell attached to either a pipette tip (FIG. 2a) or a planar substrate (FIG. 2b). The area of contact between the cell membrane and substrate surface is considerably larger in the substrate configuration (FIG. 2b) than in the pipette configuration (FIG. 2a).
Figure 3:
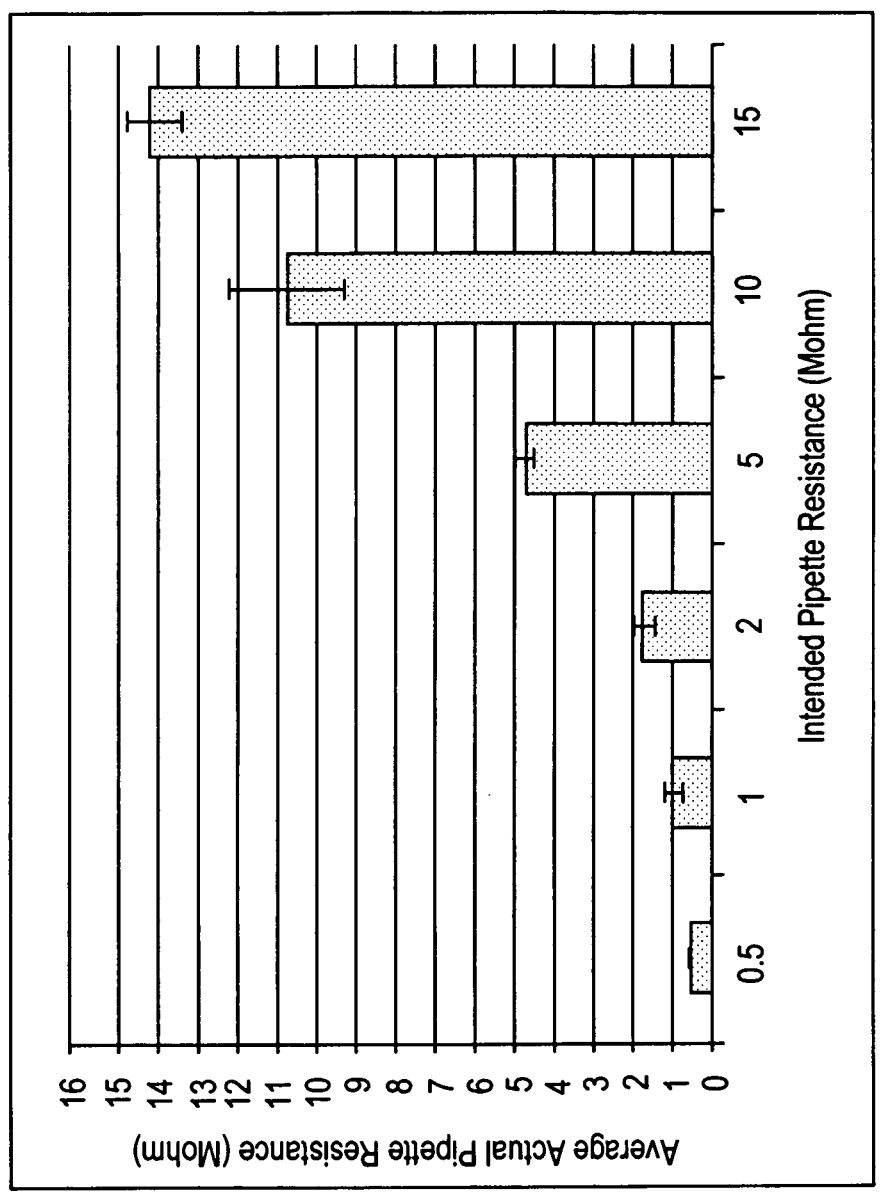
FIG. 3 shows the variation in actual pipette resistance for each intended resistance set.

To determine the optimal aperture size for obtaining gigaseal and whole cell configurations we have compared the success rates for achieving them in a standard patch-clamp set-up, using patch pipettes of varying size. The experiments were performed on HEK293 cells adhered to coverslips, immersed in sodium Ringer solution, Borosilicate capillaries (Hilgenberg, Cat No. 1403573, L=75 mm, OD=1.5 mm, ID=0.87 mm, 0.2 mm filament) were used to make pipettes. Pipette resistance was used as an indicator of relative aperture size; pipettes with intended resistances of 0.5, 1, 2, 5, 10 and 15 MΩ were fabricated. At the time of measurement, the actual pipette resistance was noted and the average actual pipette resistance for each set, along with the standard deviation from the mean, is shown in FIG. 3.

Figure 4:
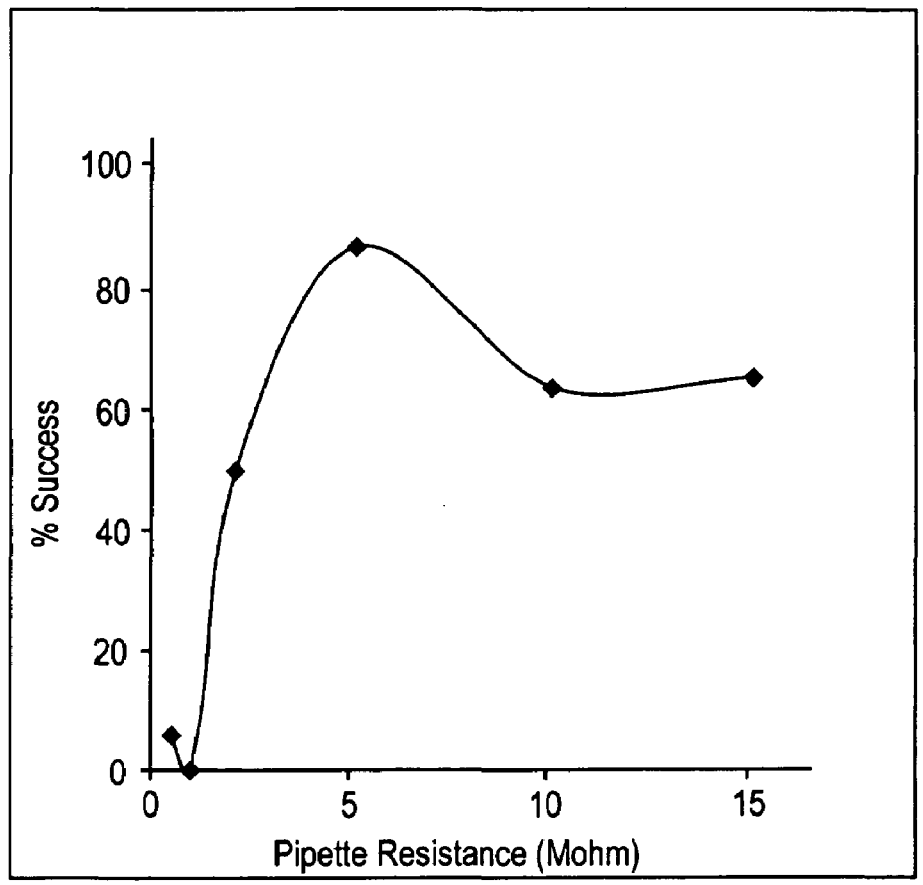
FIG. 4 shows Gigaseal success rate versus pipette resistance.

FIG. 4 shows the dependence of gigaseal and whole-cell success rates on the pipette aperture resistance aperture size). The number of experiments performed for each data set is shown above the data points. The results show that pipettes with a resistance of 5 MΩ were optimal for both gigascal formation and whole cell establishment, while resistances above 5, and up to 15 MΩ, resulted in an approximately 20% drop in the success rate. Reduction of pipette resistance below 5 MΩ was more deleterious; A resistance of 2 MΩ gave a success rate or 50%, 37% lower than for 5 MΩ, while resistances of 1 MΩ or below resulted in virtually no gigaseal formation at all.

Figure 5:
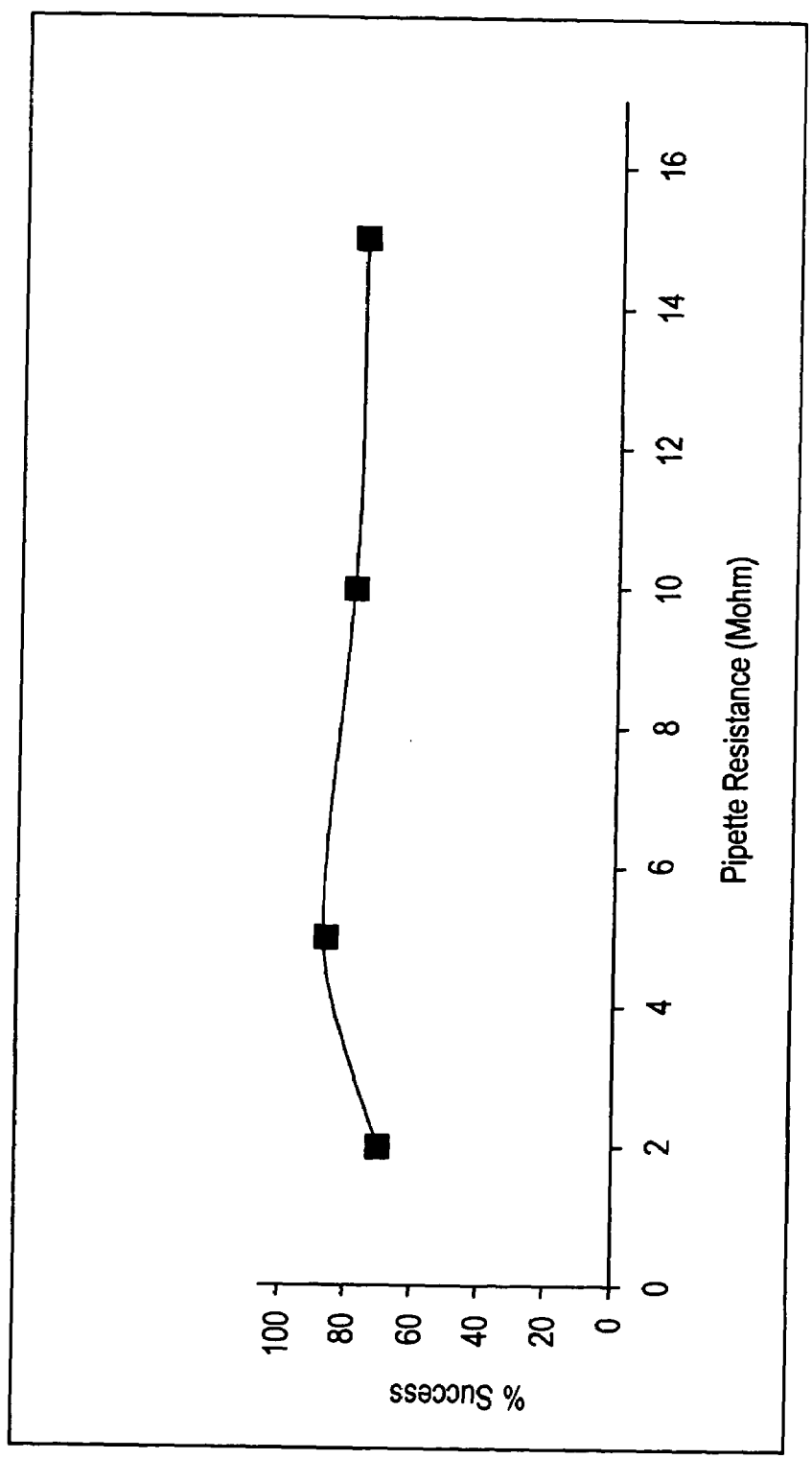
FIG. 5 shows the success rate of whole-cell establishment (from successful gigaseals) versus pipette resistance.

FIG. 5 shows the percentage of whole-cells formed from experiments in which gigaseals were successfully formed (i.e. discounting those that did not reach gigaseal). Data indicate that although 5 MΩ pipettes had the highest whole-cell success rate, the other aperture sizes had only slightly lower successes.

Figure 6:
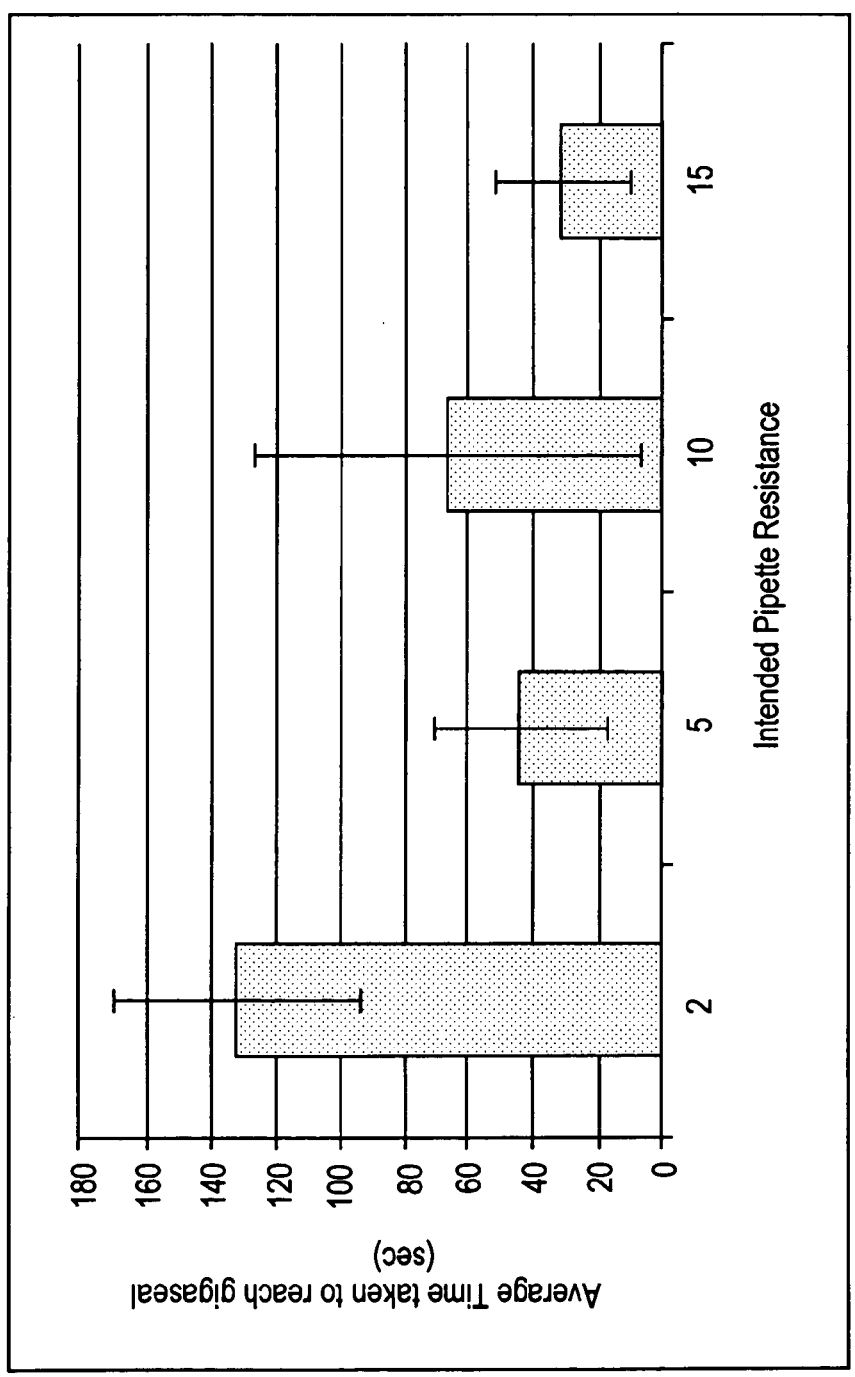
FIG. 6 shows the time-dependence of gigaseal formation with different aperture sizes, the error bars indicating the standard deviation from the mean.
Figure 7:
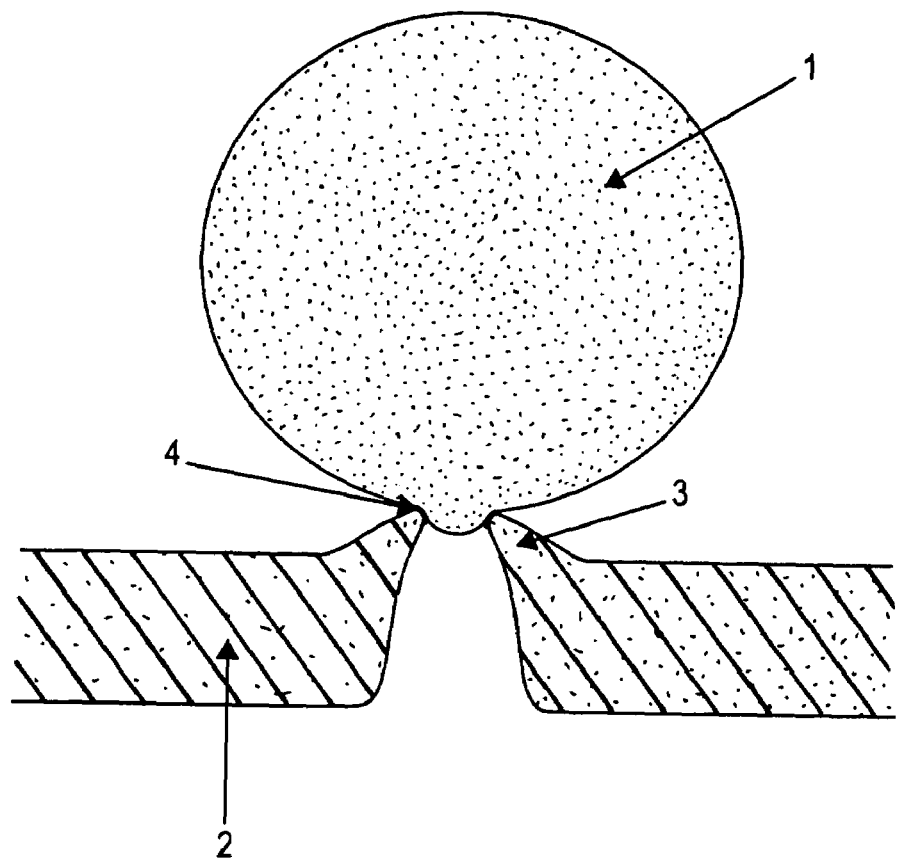
FIG. 7 shows an example of a cell attached to a planar substrate with a protruding rim flanking the aperture. The gigaseal formation zone is very confined.
Figure 8A:
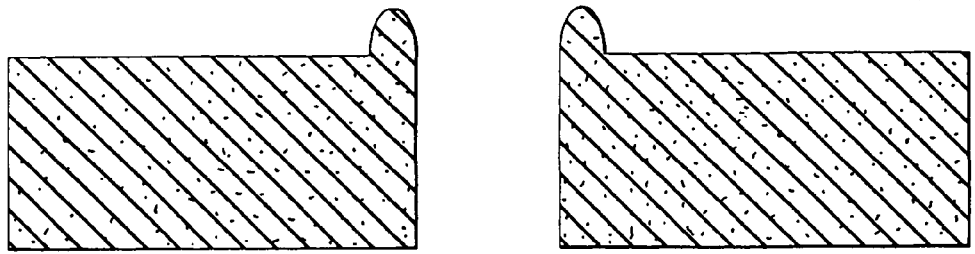
FIGS. 8a, 8b, 8c & 8d show four different aperture designs (die transactions) including a protruding rim: vertical rim (FIG. 8a); oblique rim (FIG. 8b); horizontal rim (FIG. 8c); and embedded rim (FIG. 8d).
Figure 8B:
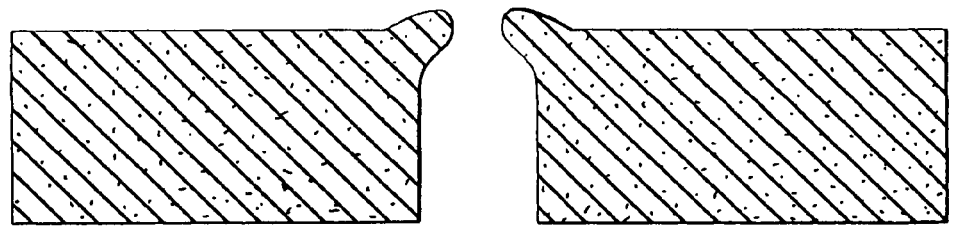
Figure 8C:
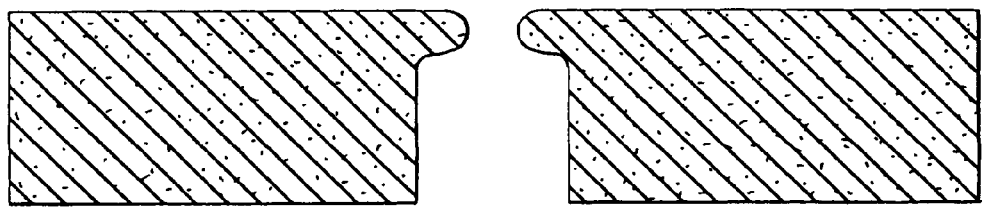
Figure 8D:
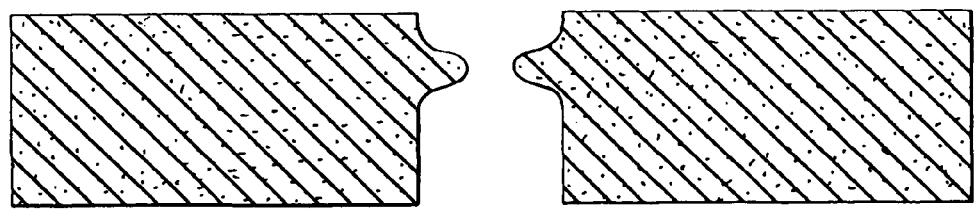

The effect of pipette resistance on the time taken to reach a GΩ resistance was also examined (see FIG. 6). The results show that the 2 MΩ pipettes took significantly longer to reach gigaseal than did pipettes of 5, 10 or 15 MΩ. The similarity of the results for the 5, 10 and 15 MΩ pipettes indicates that increasing the aperture size within this range does not affect the time take to reach gigaseal.

The results clearly show that the success of gigaseal formation is dependent on the size of the pipette aperture. The 5 MΩ pipettes had the optimal aperture size, and sizes greater than this (i.e. with lower resistances) resulted in a marked reduction is successful gigaseal formation.

Although the above experiments were performed using conventional glass micropipettes, the results can be extrapolated to planar substrates for use in patch clamp experiments. Thus, the results indicate that apertures in the chip system should, in general not measure larger than the apertures of the 5 MΩ pipettes. However, pipettes smaller than the 5 MΩ ones still performed fairly well, although they were significantly worse. Therefore, making the chip aperture slightly smaller than the 5 MΩ pipettes would be less deleterious than making it larger.

Varying the pipette aperture size appeared to have less effect on whole-cell formation. Although the success of whole-cell formation was highest in 5 MΩ pipettes, for pipettes from 2 MΩ to 15 MΩ, there was only a slight reduction in success rate.

It was also observed that the pipette aperture size had an effect on the time taken to reach a GΩ resistance. Pipettes of 5 and 15 MΩ took similar times to reach gigaseal, but those of 2 MΩ took 2.5 to 3 times longer.

Microscopy of the glass pipettes used in the experiments revealed that pipettes exhibiting 5 MΩ resistance had an aperture size of the order of 0.5–1 μm. It is, however, expected that the optimal aperture size is related to the cell type and cell size.

The success-rate for obtaining gigaseals in conventional patch clamp experiments is typically high, often around 90%, when patching cultured cells like HEK or CHO. Based on the above considerations, it is expected that comparable success-rate on planar chips may be achieved using an aperture geometry mimicking that of a conventional pipette tip orifice. Such a geometry would comprise a protruding rim flaking a 0.5 to 1 μm aperture hole. Moreover, the length (i.e. depth) of the aperture should preferably be in excess of 2 μm.

Production of Planar Patch-clamp Substrates

A preferred method of producing the planer patch-clamp substrates of tie invention is by using silicon (Si) wafer micro-fabrication and processing methods, which allow Si surfaces to be coated with silicon oxide effectively forming a high quality glass surface. Preferably, long pores and the surface modification can be made by using ICP (Inductively Coupled Plasma) and LPCVD (Low Pressure Chemical Vapour Deposition). Long apertures with a protruding rim can be made by using ICP to make the poreand RIE (Reactive Ion Etch) to form the protruding rim, combined with LPCVD to make the surface modification.

Figure 10A:
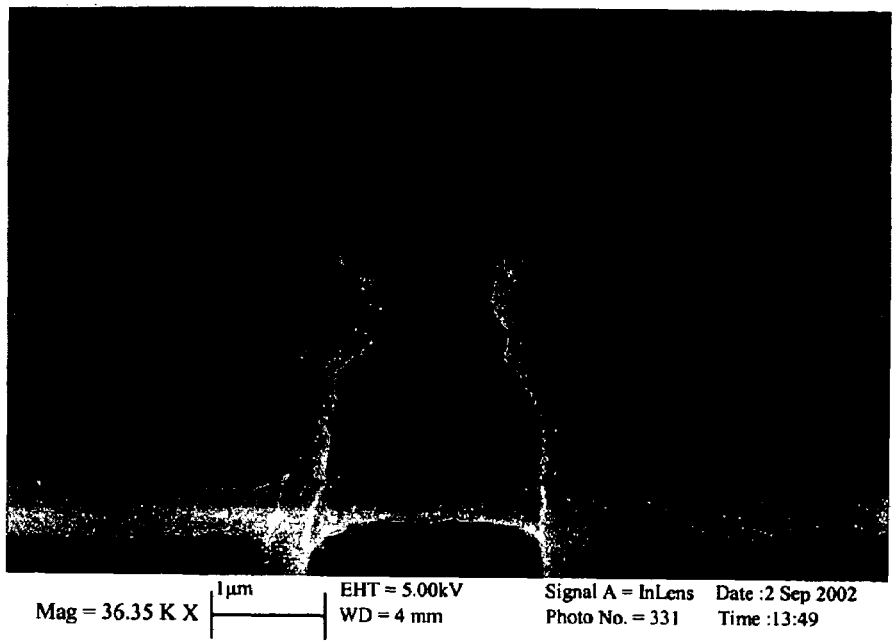
FIG. 10a and FIG. 10b are scanning electron micrographs of substrate with long pores with a protruding rim in the plane of the surface using ICP and LPCVD for surface modification.
Figure 10B:
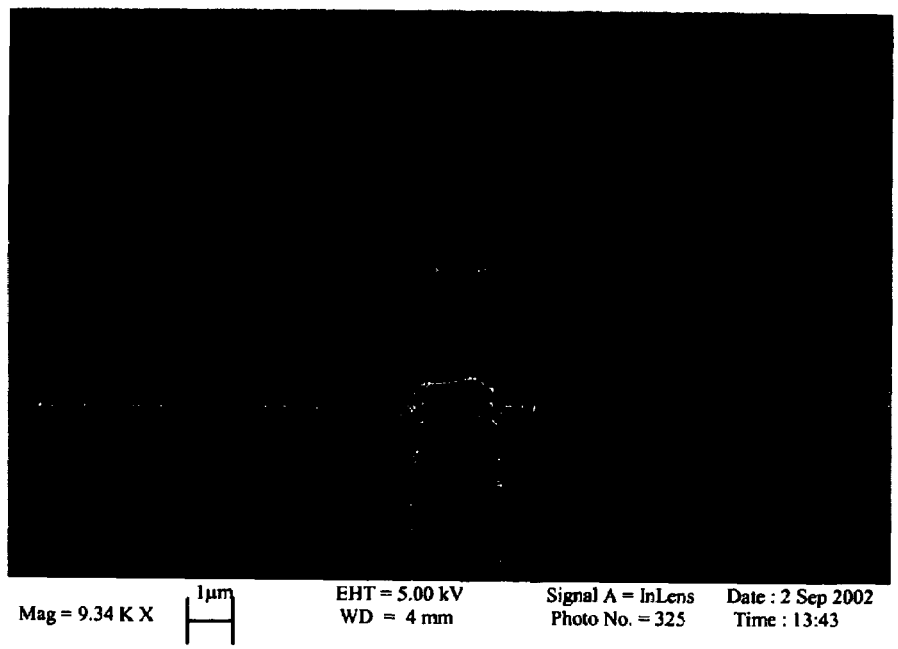

(a) Example process recipe for long apertures with a protruding rim in the plane of the surface using ICP and LPCVD for surface modification (FIG. 10a and FIG. 10b).
 1. Starting substrate: single crystal silicon wafer, crystal orientation <100>.
 2. One surface of the silicon is coated with photoresist and the pattern containing the aperture locations and diameters is transferred to the photoresist through exposure to UV light.
 3. The aperture pattern is transferred to the silicon with Deep Reactive Ion Etch (DRIE) or Advanced Silicon Etching (ASE) using an Inductively Coupled Plasma (ICP), resulting in deep vertical pores with a depth of 1–50 μm.
 4. The silicon surface is coated with a etch mask that will with stand KOH or TMAH solution. As an example this could be silicon oxide or silicon nitride.
 5. The opposite side of the wafer (the bottom side) is coated with photoresist and a pattern containing the membrane defining openings in the silicon nitride is transferred to the photoresist through exposure to UV light.
 6. The wafer is etched away on the bottom side of the wafer in the regions defined by the openings in the photoresist, using a suitable pattern transfer process. As an example this could be Reactive Ion Etch (RIE).
 7. The wafer is etched anisotropically in a KOH or TMAH solution, resulting in a pyramidal opening on the bottom side of the wafer. The timing of the etching defines the thickness of the remaining membrane of silicon at the topside of the wafer. Alternatively boron doping can be used to define an etch stop, giving a better control of the thickness.
 8. The etch mask is remove selectively to the silicon substrate.
 9. The silicon is coated with silicon oxide, either through thermal oxidation, with plasma enhanced chemical vapor deposition (PECVD) or with LPCVD.

Alternatively the substrate can be fabricated through the following process:
 1. Starting substrate: single crystal silicon wafer.
 2. One surface of the silicon is coated with photoresist and the pattern containing the aperture locations and diameters is transferred to the photoresist through exposure to UV light.
 3. The aperture pattern is transferred to the silicon with Deep Reactive Ion Etch (DRIE) or Advanced Silicon Etching (ASE) using an Inductively Coupled Plasma (ICP), resulting in deep vertical pores with a depth of 1–50 μm.
 4. The opposite side of the wafer (the bottom side) is coated with photoresist and a pattern containing the membrane definitions is transferred to the photoresist through exposure to UV light.
 5. The wafer is etched anisotropically using Deep Reactive Ion Etch (DRIE) or Advanced Silicon Etching (ASE) using an Inductively Coupled Plasma (ICP), resulting in a cylindrical opening on the bottom side of the wafer. The timing of the etching defines the thickness of the remaining membrane of silicon at the topside of the wafer.
 6. The silicon is coated with silicon oxide, either through thermal oxidation, with plasma enhanced chemical vapor deposition (PECVD) or with LPCVD.

Alternatively the substrate can be fabricated through the following process:
 1. Starting substrate: silicon on insulator (SOI) with a buried oxide layer located 1–50 μm below the top surface, carrier crystal orientation <100>.
 2. One surface of the silicon is coated with photoresist and the pattern containing the aperture locations and diameters is transferred to the photoresist through exposure to UV light.
 3. The aperture pattern is transferred to the silicon with Deep Reactive Ion Etch (DRIE) or Advanced Silicon Etching (ASP) using an Inductively Coupled Plasma (ICP), resulting in deep vertical pores down to the depth of the buried oxide layer.
 4. The silicon surface is coated with a etch mask that will with stand KOH or TMAH solution. As an example this could be silicon oxide or silicon nitride.
 5. The opposite side of the wafer (the bottom side) is coated with photoresist and a pattern containing the membrane defining openings in the silicon nitride is transferred to the photoresist through exposure to UV light.
 6. The wafer is etched away on the bottom side of the wafer in the regions defined by the openings in the photoresist, using a suitable pattern transfer process. As an example this could be Reactive Ion Etch (RIE).
 7. The wafer is etched anisotropically in a KOH or TMAH solution, resulting in a pyramidal opening on the bottom side of the wafer. The buried oxide will act as an etch stop for the process, hence thickness of the topside silicon layer defines the thickness of the remaining membrane.
 8. The exposed regions of the buried oxide layer are removed through RIE, wet hydrofluoric acid (HF) etch, or HF vapor etch. This will ensure contact between the top and bottom openings in the wafer.
 9. The etch mask is remove selectively to the silicon substrate.
 10. The silicon is coated with silicon oxide, either through thermal oxidation, with plasma enhanced chemical vapor deposition (PECVD) or with LPCVD.

Alternatively the substrate can be fabricated through the following process.
1. Starting substrate: silicon on insulator (SOI) with a buried oxide layer located 1–50 μm below the top surface.
2. One surface of the silicon is coated with photoresist and the pattern containing the aperture locations and diameters is transferred to the photoresist through exposure to UV light.
3. The aperture pattern is transferred to the silicon with Deep Reactive Ion Etch (DRIE) or Advanced Silicon Etching (ASE) using an Inductively Coupled Plasma (ICP), resulting in deep vertical pores down to the depth of the buried oxide layer.
4. The opposite side of the wafer (the bottom side) is coated with photoresist and a pattern containing the membrane definitions is transferred to the photoresist through exposure to UV light.
5. The wafer is etched anisotropically using Deep Reactive Ion Etch (DRIE) or Advanced Silicon Etching (ASE) using an Inductively Coupled Plasma (ICP), resulting in vertical cavities on the bottom side of the wafer. The buried oxide will act as an etch stop for the process, hence thickness of the topside silicon layer defines the thickness of the remaining membrane.
6. The exposed regions of the buried oxide layer are removed through RIE, wet hydrofluoric acid (HF) etch, or HF vapor etch. This will ensure contact between the top and bottom openings in the wafer.
7. The silicon is coated with silicon oxide, either through thermal oxidation, with plasma enhanced chemical vapor deposition (PECVD) or with LPCVD.

Alternatively the substrate can be fabricated through the following process:
1. Starting substrate: glass or pyrex wafer.
2. One surface of the silicon is coated with photoresist and the pattern containing the aperture locations and diameters is transferred to the photoresist through exposure to UV light.
3. The aperture pattern is transferred to the wafer with Deep Reactive Ion Etch (DRIE) or Advanced Oxide Etching (AOE) using an Inductively Coupled Plasma (ICP), resulting in deep vertical pores with a depth of 1–50 μm.
4. The opposite side of the wafer (the bottom side) is coated with photoresist and a pattern containing the membrane definitions is transferred to the photoresist through exposure to UV light.
5. The wafer is etched anisotropically using Deep Reactive Ion Etch (DRIE) or Advanced Oxide Etching (AOE) using an Inductively Coupled Plasma (ICP), resulting in vertical cavities on the bottom side of the wafer. The timing of the etching defines the thickness of the remaining membrane of glass or pyrex at the topside of the wafer.
6. The silicon is coated with silicon oxide, either through thermal oxidation, with plasma enhanced chemical vapor deposition (PECVD) or with LPCVD.

We have not demonstrated the process with glass wafers.

Figure 11:
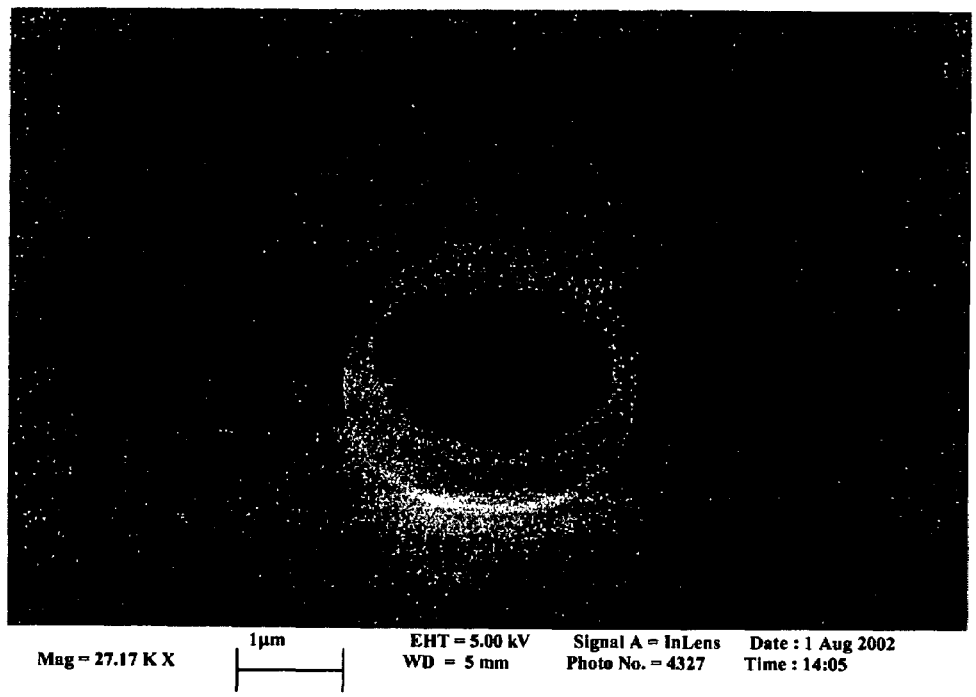
FIG. 11 is a scanning electron micrograph of a substrate with long pores with a protruding rim out of the plane of the surface using ICP and LPCVD for surface modification.

(b) Example process recipe for long pores with a protruding rim out of the plane of the surface using ICP and LPCVD for surface modification (FIG. 11)
1. Starting substrate: single crystal silicon wafer, crystal orientation <100>.
2. One surface of the silicon is coated with photoresist and the pattern containing the aperture locations and diameters is transferred to the photoresist through exposure to UV light.
3. The aperture pattern is transferred to the silicon with Deep Reactive Ion Etch (DRIE) or Advanced Silicon Etching (ASE) using an Inductively Coupled Plasma (ICP), resulting in deep vertical pores with a depth of 1–50 μm.
4. The silicon surface is coated with silicon nitride using Low Pressure Chemical Vapour Deposition (LPCVD) or Plasma Enhanced Chemical Vapour Deposition (PECVD).
5. The opposite side of the wafer (the bottom side) is coated with photoresist and a pattern containing the membrane defining openings in the silicon nitride is transferred to the photoresist through exposure to UV light.
6. The silicon nitride is etched away on the bottom side of the wafer in the regions defined by the openings in the photoresist, using Reactive Ion Etch (RIE).
7. The wafer is etched anisotropically in a KOH or TMAH solution, resulting in a pyramidal opening on the bottom side of the wafer. The timing of the etching defines the thickness of the remaining membrane of silicon at the topside of the wafer. Alternatively boron doping can be used to define an etch stop, giving a better control of the thickness.
8. RIE on rear side, removing the Si-nitride mask on the rear side of the wafer and opening the rear end of the aperture.
9. RIE on front side, removing the Si-nitride on the front side leaving a protruding Si-nitride rim on the orifice.
10. The silicon is coated with silicon oxide, either through thermal oxidation, with plasma enhanced chemical vapor deposition (PECVD) or with LPCVD.

Alternatively the substrate can be fabricated through the following process:
1. Starting substrate: single crystal silicon wafer.
2. One surface of the silicon is coated with photoresist and the pattern containing the aperture locations and diameters is transferred to the photoresist through exposure to UV light.
3. The aperture pattern is transferred to the silicon with Deep Reactive Ion Etch (DRIE) or Advanced Silicon Etching (ASE) using an Inductively Coupled Plasma (ICP), resulting in deep vertical pores with a depth of 1–50 μm.
4. The silicon surface is coated with silicon nitride using Low Pressure Chemical Vapour Deposition (PCVD) or Plasma Enhanced Chemical Vapour Deposition (PECVD).
5. The opposite side of the wafer (the bottom side) is coated with photoresist and a pattern containing the membrane defining openings in the silicon nitride is transferred to the photoresist through exposure to UV light.
6. The silicon nitride is etched away on the bottom side of the wafer in the regions defined by the openings in the photoresist, using Reactive Ion Etch (RIE).
7. The wafer is etched anisotropically using Deep Reactive Ion Etch (DRIE) or Advanced Silicon Etching (ASE) using an Inductively Coupled Plasma (ICP), resulting in a cylindrical opening on the bottom side of the wafer. The timing of the etching defines the thickness of the remaining membrane of silicon at the topside of the wafer.

8. RIE on rear side, removing the Si-nitride mask on the rear side of the wafer and opening the rear end of the aperture.
9. RIE on front side, removing the Si-nitride on the front side leaving a protruding Si-nitride rim on the orifice.
10. The silicon is coated with silicon oxide, either through thermal oxidation, with plasma enhanced chemical vapor deposition (PECVD) or with LPCVD.

Alternatively the substrate can be fabricated through the following process:

1. Starting substrate: silicon on insulator (SOI) with a buried oxide layer located 1–50 μm below the top surface, carrier crystal orientation <100>.
2. One surface of the silicon is coated with photoresist and the pattern containing the aperture locations and diameters is transferred to the photoresist through exposure to UV light.
3. The aperture pattern is transferred to the silicon with Deep Reactive Ion Etch (DRIE) or Advanced Silicon Etching (ASE) using an Inductively Coupled Plasma (ICP), resulting in deep vertical pores down to the depth of the buried oxide layer.
4. The silicon surface is coated with silicon nitride using Low Pressure Chemical Vapour Deposition (LPCVD) or Plasma Enhanced Chemical Vapour Deposition (PECVD).
5. The opposite side of the wafer (the bottom side) is coated with photoresist and a pattern containing the membrane defining openings in the silicon nitride is transferred to the photoresist through exposure to UV light.
6. The silicon nitride is etched away on the bottom side of the wafer in the regions defined by the openings in the photoresist, using Reactive Ion Etch (RIE).
7. The wafer is etched anisotropically in a KOH or TMAH solution, resulting in a pyramidal opening on the bottom side of the wafer. The buried oxide will act as an etch stop for the process, hence thickness of the topside silicon layer defines the thickness of the remaining membrane.
8. The exposed regions of the buried oxide layer are removed through RIE, wet hydrofluoric acid (HF) etch, or HF vapor etch. This will ensure contact between the top and bottom openings in the wafer.
9. RIE on rear side, removing the Si-nitride mask on the rear side of the wafer and opening the rear end of the aperture.
10. RIE on front side, removing the Si-nitride on the front side leaving a protruding Si-nitride rim on the orifice.
11. The silicon is coated with silicon oxide, either through thermal oxidation, with plasma enhanced chemical vapor deposition (PECVD) or with LPCVD.

Alternatively the substrate can be fabricated through the following process:

1. Starting substrate: silicon on insulator (SOI) with a buried oxide layer located 1–50 μm below the top surface.
2. One surface of the silicon is coated with photoresist and the pattern containing the aperture locations and diameters is transferred to the photoresist through exposure to UV light.
3. The aperture pattern is transferred to the silicon with Deep Reactive Ion Etch (DRIE) or Advanced Silicon Etching (ASE) using an Inductively Coupled Plasma (ICP), resulting in deep vertical pores down to the depth of the buried oxide layer.
4. The silicon surface is coated with silicon nitride using Low Pressure Chemical Vapour Deposition (LPCVD) or Plasma Enhanced Chemical Vapour Deposition (PECVD).
5. The opposite side of the wafer (the bottom side) is coated with photoresist and a pattern containing the membrane defining openings in the silicon nitride is transferred to the photoresist through exposure to UV light.
6. The silicon nitride is etched away on the bottom side of the wafer in the regions defined by the openings in the photoresist, using Reactive Ion Etch (RIE).
7. The wafer is etched anisotropically using Deep Reactive Ion Etch (DRIE) or Advanced Silicon Etching (ASE) using an Inductively Coupled Plasma (ICP), resulting in vertical cavities on the bottom side of the wafer. The buried oxide will act as an etch stop for the process, hence thickness of the topside silicon layer defines the thickness of the remaining membrane.
8. The exposed regions of the buried oxide layer are removed through RIE, wet hydrofluoric acid (HF) etch, or HF vapor etch. This will ensure contact between the top and bottom openings in the wafer.
9. RIE on rear side, removing the Si-nitride mask on the rear side of the wafer and opening the rear end of the aperture.
10. RIE on front side, removing the Si-nitride on the front side leaving a protruding Si-nitride rim on the orifice.
11. The silicon is coated with silicon oxide, either through thermal oxidation, with plasma enhanced chemical vapor deposition (PECVD) or with LPCVD.

REFERENCES

Mayer, M (2000). Screening for bioactive compounds: Chip-based functional analysis of single ion channels & capillary electrochromatography for immunoaffinity selection. Ph.D thesis, Lausanne.

Neher, E (2001). Molecular biology meets microelectronics. Nature Biotechnology 19:114.

Penner, R (1995). A practical guide to patch clamping. In: Single-Channel Recording. (Ed. E Neher) Plenum Press, New York, London.

Rae, J and Levis, R A (1992). Glass technology for patch clamp electrodes. Methods Enzymol. 207;66–92.

Simons, K and Toomre, D (2000) Lipid rafts and signal transduction. Nature Reviews 1:31–41.

Madou, M., "Fundamentals of Microfabrication", 2nd Ed (December 2001) CRC Press; ISBN: 0849308267

Laermer F.; Schilp, A., "Method of anisotropically etching silicon", Patent DE4241045 (also U.S. Pat. No. 5,501,893, WO94/14187)

The invention claimed is:

1. A substantially planar substrate for use in patch clamp analysis of the electrophysiological properties of a cell membrane comprising a glycocalyx, wherein the substrate comprises an aperture having a rim adapted to form a gigaseal upon contact with the cell membrane, the rim protruding from a plane of the substrate to a length in excess of a thickness of the glycocalyx and being formed from the same material as that of the substrate.

2. The planar substrate according to claim 1, wherein the rim protrudes from the substrate to a length of at least 20 nm from the surface of the planar substrate, or at least 30 nm, at least 40 nm, at least 50 nm, at least 60 nm, at least 70 nm, at least 80 nm, at least 90 nm or at least 100 nm.

3. The planar substrate according to claim 1, wherein the width of the rim is in the range 10 to 200 nm.

4. The planar substrate according to claim 1, in which the length (i.e. depth) of the aperture is between 2 and 30 μm, 2 and 20 μm, 2 and 10 μm, or 5 and 10 μm.

5. The planar substrate according claim 1, wherein the diameter of the aperture is in the range 0.5 to 2 μm.

6. The planar substrate according to claim 1, wherein the rim extends substantially perpendicularly to the plane of the substrate.

7. The substrate according to claim 1, wherein the rim forms an oblique angle with the plane of the substrate.

8. The substrate according to claim 1, wherein the rim is substantially parallel to the plane of the substrate.

9. The substrate according to claim 1, wherein the rim is defined by a mouth of the aperture, which mouth has a radius of curvature between 5 and 100 nm with an angle of 45 to 90 degrees.

10. The planar substrate according to claim 1, wherein the substrate is made of silicon, plastics, pure silica or other glasses, such as quartz and Pyrex™, or silica doped with one or more dopants selected from the group consisting of Be, Mg, Ca, B, Al, Ga, Ge, N, P, As.

11. The planar substrate according to claim 10, wherein the substrate is made of silicon.

12. The substrate according to claim 1, wherein a surface of the substrate and/or walls of the aperture are coated with a second coating material.

13. The substrate according to claim 12, wherein the coating material is silicon, plastics, pure silica, other glasses such as quartz and Pyrex™, silica doped with one or more dopants selected from the group consisting of Be, Mg, Ca, B, Al, Ga, Ge, N, P, As, or oxides of the same.

14. The substrate according to claim 10, wherein the coating material is silicon oxide.

15. A method of making a substantially planar substrate for use in patch clamp analysis of the electrophysiological properties of a cell membrane comprising a glycocalyx, wherein the substrate comprises an aperture having a rim adapted to form a gigaseal upon contact with the cell membrane, the method comprising the steps of:
 (i) providing a substrate template;
 (ii) forming the aperture in the template; and
 (iii) forming the rim from the same material as that of the substrate in which the aperture is formed such that the rim protrudes from the substrate to a length in excess of the thickness of the glycocalyx.

16. The method according to claim 15, wherein the substrate is manufactured using silicon micro fabrication technology.

17. The method according to claim 15, wherein step (ii) comprises forming an aperture by use of an inductively coupled plasma (ICP) deep reactive ion etch process.

18. The method according to claim 15, further comprising the step of coating a surface of the substrate.

19. The method according to claim 18, wherein step (iii) is performed at the same time as coating the substrate.

20. The method according to claim 18, wherein step (iii) comprises an intermediate step of a directional and selective etching of a front side of the substrate causing a removal of a masking layer on the front side of the substrate, and further proceeding a prescribed protrusion distance into the underlying substrate.

21. The method according to claim 18, wherein the coating is deposited by use of plasma enhanced chemical vapour deposition (PECVD) and/or by use of low pressure chemical vapour deposition (LPCVD).

22. The method according to claim 21, wherein the coating is deposited by use of plasma enhanced chemical vapour deposition (PECVD).

23. The method according to claim 17, wherein step (iii) comprises forming a rim from a deposited surface coating by use of plasma enhanced chemical vapour deposition (PECVD).

24. A method for analysing the electrophysiological properties of a cell membrane comprising a glycocalyx, the method comprising the following steps:
 (i) making a substantially planar substrate for use in patch clamp analysis of electrophysiological properties of a cell membrane comprising a glycocalyx, wherein the substrate comprises an aperture having a rim adapted to form a gigaseal upon contact with the cell membrane, the method comprising the steps of
  (a) providing a substrate template,
  (b) forming the aperture in the template, and
  (c) forming the rim from the same material as that of the substrate in which the aperture is formed such that the rim protrudes from the substrate to a length in excess of the thickness of the glycocalyx;
 (ii) contacting the cell membrane with the rim of an aperture of the substrate such that the gigaseal is formed between the cell membrane and the substrate; and
 (iii) measuring the electrophysiological properties of the cell membrane.

25. A kit for performing a method according to claim 24, the kit comprising a substantially planar substrate for use in patch clamp analysis of electrophysiological properties of a cell membrane comprising a glycocalyx, wherein the substrate comprises an aperture having a rim adapted to form a gigaseal upon contact with the cell membrane, the rim protruding from the substrate to a length in excess of a thickness of the glycocalyx and being formed from the same material as that of the substrate and one or more media or reagents for performing pitch clamp studies.

* * * * *